United States Patent [19]

Rupp et al.

[11] Patent Number: 5,382,599
[45] Date of Patent: Jan. 17, 1995

[54] METHOD OF INHIBITING PROTOZOAN GROWTH IN EYE CARE PRODUCTS USING A POLYVALENT CATION CHELATING AGENT

[75] Inventors: David C. Rupp, San Pedro; Claude Anger, Long Beach; Saroj Kapadia, Irvine; Mary Totaro, Cypress, all of Calif.

[73] Assignee: Allergan, Inc., Irvine, Calif.

[21] Appl. No.: 136,517

[22] Filed: Oct. 13, 1993

[51] Int. Cl.⁶ ............................................. A61K 31/225
[52] U.S. Cl. ..................................... 514/547; 514/912
[58] Field of Search ................................ 514/547, 912

[56] References Cited

U.S. PATENT DOCUMENTS

| | | | |
|---|---|---|---|
| 3,767,788 | 10/1973 | Rankin | 424/78 |
| 3,882,036 | 5/1975 | Krezanoski et al. | 252/106 |
| 3,907,985 | 9/1975 | Rankin | 424/78 |
| 4,039,662 | 8/1977 | Hecht et al. | 424/180 |
| 4,104,187 | 8/1978 | Sibley et al. | 252/106 |
| 4,131,696 | 12/1978 | Covington | 427/164 |
| 4,152,283 | 5/1979 | Cordrey et al. | 252/99 |
| 4,188,394 | 2/1980 | Eakins et al. | 424/262 |
| 4,190,673 | 2/1980 | Eakins et al. | 424/324 |
| 4,197,301 | 4/1980 | Smith et al. | 424/251 |
| 4,230,724 | 10/1980 | Cooper et al. | 424/317 |
| 4,323,467 | 4/1982 | Fu | 252/106 |
| 4,367,157 | 1/1983 | Sherman | 252/106 |
| 4,401,582 | 8/1983 | Sherman | 252/90 |
| 4,409,205 | 10/1983 | Shively | 424/78 |
| 4,474,811 | 10/1984 | Masuda et al. | 424/317 |
| 4,499,077 | 2/1985 | Stockel et al. | 424/149 |
| 4,525,346 | 6/1985 | Stark | 424/80 |
| 4,551,461 | 11/1985 | Sherman | 514/275 |
| 4,597,965 | 7/1986 | Holly | 424/81 |
| 4,607,038 | 8/1986 | Ogata et al. | 514/291 |
| 4,615,882 | 10/1986 | Stockel | 424/80 |
| 4,654,208 | 3/1987 | Stockel et al. | 424/78 |
| 4,748,189 | 5/1988 | Su et al. | 514/781 |
| 4,880,601 | 11/1989 | Andermann et al. | 422/28 |
| 4,960,799 | 10/1990 | Nagy | 514/567 |
| 5,032,392 | 7/1991 | Varma | 424/78 |
| 5,037,647 | 8/1991 | Chowhan et al. | 424/78 |
| 5,110,493 | 5/1992 | Cherng-Chyi et al. | 514/413 |

OTHER PUBLICATIONS

WPI Acc No: 92-233948/28 (1985). Washman.
Ma, P.; Visvesvara, G. S.; Martinez, A. J.; Theodore, F. H.; Daggett, P-M.; Sawyer, T. K.; "Naegleria and Acanthamoeba Infections: Review"; Reviews of Infectious Diseases; 1990 May/Jun.; 12(3):490-513.
Neff, R. J.; Ray, S. A.; Benton, W. F.; Wilborn, M.; "Induction of Synchronous Encystment (Differentiation) in Acanthamoeba sp."; Methods in Cell Physiology, vol. 1, Ch. 4, pp. 55-83 (D. M. Prescott. Ed., Academic Press, New York 1977).
Martinez, A. J.; "Free-Living Amoebae: Pathogenic Aspects a Review"; Protozoological Abstracts, 1983 vol. 7, No. 7.
Moore, M. B.; "Acanthamoeba Keratitis Associated with Contact Lens Wear"; Contact Lenses: Update 4; 42A 1-17. (1989).

Primary Examiner—Zohreh Fay

[57] ABSTRACT

A method for inhibiting the growth of protozoa in an eye care product is disclosed. The method includes the step of adding to the eye care product an effective protozoan growth-inhibiting amount of a polyvalent cation chelating agent. Methods are also disclosed for inhibiting the growth of protozoa on a surface of an eye care product by contacting the surface with a solution including an effective protozoan growth-inhibiting amount of a polyvalent cation chelating agent. Eye care products containing protozoan growth-inhibiting agents are also disclosed.

18 Claims, No Drawings

METHOD OF INHIBITING PROTOZOAN GROWTH IN EYE CARE PRODUCTS USING A POLYVALENT CATION CHELATING AGENT

FIELD OF THE INVENTION

The present invention relates to a method of inhibiting the growth of protozoa in eye care products such as ophthalmic solutions and on the surfaces of eye care products such as contact lenses.

BACKGROUND OF THE INVENTION

Eye care products, such as contact lens care systems, are susceptible to contamination by ocular pathogens. Known ocular pathogens include bacteria, fungi, and also protozoans such as amoebae, for example the acanthamoebae. Acanthamoebae are ubiquitous free-living protozoans, which exist in two distinct morphological forms: the trophozoite and the cyst. The trophozoite form is the free swimming form and is relatively easy to kill. The organism encysts in an adverse environment, creating a thick protective coat making it very difficult, to kill. The cyst form is the hibernating form of the organism. The organism reverts to the trophozoite form in a favorable environment.

A variety of species of Acantharnoeba have been found to cause infectious keratitis. These species include *A. polyphaga, A. castellanii, A. lenticulata, A. hatchetti, A. astronyxis, A. culbertsoni, A. rhysodes,* and others. See, for example, Ma et al., Rev. Infectious Diseases 1990 May/June; 12(3):490-513 and the references cited therein. Moreover, acanthamoebae use bacteria and fungi as a food source. Co-contamination of contact lens care system with bacteria and fungi facilitates the growth of the acanthamoebae in the contact lens care system, and is thus implicated as a risk factor for acanthamoebic keratitis.

The incidence of ulcerative keratitis among soft contact lens wearers in the United States has been found to be a function of contact lens wear mode. An incidence of infection of 4.1 per 10,000 daily wear patients per year and 20.9 per 10,000 extended wear patients per year has been found. Thus of the approximately 20 million contact lens wearers in the United States, over 12,000 infections (from all causes) occur yearly. Acanthamoebic keratitis has been reported in contact lens wearers regardless of lens type.

Various agents have been found to be effective in killing and/or inhibiting the growth of bacteria or fungi. For example, U.S. Pat. No. 4,499,077 to Stockel discloses an antimicrobial composition for soft contact lenses including an oxidizing agent such as an oxyhalogen compound, e.g., stabilized chlorine dioxide or hydrogen peroxide, and a polymeric germicide, e.g., a quaternary ammonium polymer or an amino and/or imino polymer or salts thereof. U.S. Pat. No. 4,654,208 to Stockel discloses an antimicrobial composition for contact lenses including an aqueous solution of a germicidal polymeric nitrogen compound and an oxidizing agent, e.g., chlorine dioxide, chlorite, stabilized chlorine dioxide or hydrogen peroxide, to potentiate the activity of the germicidal polymeric nitrogen compound at low concentrations. However, no agents have been proposed as effective in inhibiting the growth of protozoans.

It would be desirable to inhibit the growth of protozoans such as acanthamoebae in eye care products such as contact lens solutions, in order to reduce the incidence of acanthamoebic keratitis and other ophthalmic pathologies due to the presence of protozoans.

SUMMARY OF THE PREFERRED EMBODIMENTS

Polyvalent cation chelating agents, such as EDTA, have been employed in many ophthalmic and contact lens case formulations to increase the stability of the formulations or to enhance the activity of preservative/disinfectant systems. Applicants have now surprisingly discovered that such chelating agents are also effective per se in inhibiting the growth of protozoans, including amoebae such as acanthamoebae.

In accordance with one aspect of the present invention, there has been provided a method for inhibiting the growth of protozoa in an eye care product which comprises the step of adding to the eye care product an effective protozoan growth-inhibiting amount of a polyvalent cation chelating agent.

In a preferred embodiment, the polyvalent cation chelating agent is selected from the group consisting of ethylenediamine tetraacetate (EDTA), cyclohexanediamine tetraacetate (CDTA), hydroxyethylethylenediamine triacetate (HEDTA), diethylenetriamine pentaacetate (DTPA), 1,2-diaminocyclohexane tetraacetate, and hexametaphosphate. These agents preferably are employed as salts, typically sodium salts such as disodium EDTA, trisodium HEDTA, sodium hexametaphosphate, etc. Very preferably, the chelating agent is EDTA.

In accordance with another aspect of the present invention, a method for inhibiting the growth of protozoa on a surface of an eye care product is provided which comprises the step of contacting the eye care product with a solution comprising an effective amount of a polyvalent cation chelating agent.

In accordance with still another aspect of the present invention, an eye care product is provided which includes an effective amount of a protozoan growth-inhibiting agent consisting essentially of a polyvalent cation chelating agent.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

DETAILED DESCRIPTION OF PREFERRED EMBODIMENTS

The present invention is directed to a method for inhibiting the growth of protozoa in or on the surface of an eye care product by contacting the eye care product with an effective protozoan growth-inhibiting amount of a polyvalent cation chelating agent.

As used herein, a "polyvalent cation chelating agent" is an agent capable of forming coordination bonds with a cation having a positive charge of at least 2. Such cations include, for example, $Ca^{2+}$, $Mg^+$, $Fe^{2+}$, $Fe^{3+}$, $Mn^{2+}$, $Zn^{2+}$, $Cu^{2+}$ and $Ni^{2+}$. Combinations of two or more such agents are also included within the scope of this term. The term "protozoan growth-inhibiting agent" in the context of an eye care product of the invention denotes a polyvalent cation chelating agent or combinations of such agents as described above.

In protozoan cells, particularly acanthamoebal cells, polyvalent cations such as calcium, magnesium, iron, manganese, and zinc serve as cofactors of enzymes required for metabolism. These polyvalent cations also affect the function and structure of the trophozoite by influencing the tonicity of the environment. Calcium and magnesium have been shown in the literature to be essential for acanthamoeba encystment. See Neff et al., "Induction of Synchronous Encystment (Differentiation) in Acanthamoeba sp.," Methods in Cell Physiology, vol. 1, ch. 4, pp. 55–83 (D. M. Prescott, ed., Academic Press, New York 1977). Calcium salts have also been shown to affect acanthamoeba ameboid locomotion and attachment.

Applicants have thus found that the use of polyvalent cation chelating agents effectively inhibits protozoan cell functions, particularly cell growth, which require such cations. Prior to applicants' discovery, it was not suspected that a polyvalent cation chelating agent, such as EDTA, would have an inhibiting effect per se against the growth of microorganisms, particularly protozoans such as acanthamoebae.

As used herein, a polyvalent cation chelating agent "effectively inhibits" protozoan growth if exposure of a known initial number of protozoa to the agent over a period of at least seven days results in a constant or reduced number of protozoa. Inhibition of protozoan growth includes in particular prevention of excystment of the protozoa.

Preferred chelating agents are those which are ophthalmically acceptable, and include EDTA, CDTA, HEDTA, DTPA, 1,2-diaminocyclohexane tetraacetate, and hexametaphosphate. Very preferably, the chelating agent is EDTA. The chelating agent can be employed in the form of an ophthalmically acceptable salt, such as disodium EDTA.

The amount of chelating agent employed is sufficient to inhibit the growth of protozoans. The minimum amount of chelating agent is that amount at which growth inhibition becomes observable, for example after an exposure time of about seven days. The maximum amount is the maximum ophthalmically acceptable amount, i.e., the amount beyond which the eye begins to suffer harm. Preferably the chelating agent is employed in an amount from about 0.05 to 0.5 wt % in solution. Solid formulations, such as tablets, will include proportions of chelating agents sufficient to afford the desired percentage upon dissolution in an appropriate liquid medium such as saline.

The invention is effective in inhibiting the growth of protozoans including, but not limited to, acanthamoebae, for example *A. polyphaga, A. castellani, A. lenticulata, A. hatchetti, A. astronyxis, A. culbertsoni,* and *A. rhysodes.* The invention is also effective in inhibiting the growth of other protozoans, such as amoebae of the genus Naegleria.

The invention can be practiced utilizing many well-known types of eye care products, including but not limited to saline solutions, rinsing solutions, neutralizing solutions, cleaning solutions such as enzymatic cleaning solutions, disinfecting solutions, storage solutions and lubricating/wetting solutions. Such solutions can contain, in addition to a chelating agent according to the present invention, additives and excipients well known to those skilled in the art. These additives include, without limitation: saline solutions, typically those having a pH in the range of about 6 to 8; surfactants including cationic, anionic, nonionic or amphoteric surfactants such as polyethylene glycol esters of fatty acids, polyoxypropylene ethers of $C_{12}$–$C_{18}$ alkanes, polyethylene glycol fatty alcohol ethers such as PEG 24 ® polyoxyethylene sorbitan fatty acid esters such as polyoxyethylene sorbitan monooleate (Polysorbate 80 ® trademark of Atlas Chemical Company), and polyoxyethylene, polyoxypropylene block copolymers of ethylene diamine (i.e. polyoxamine); tonicity adjusting agents such as sodium and potassium chloride, propylene glycol, and dextrose; buffering agents such as sodium or potassium acetates, borates, phosphates, and citrates, citric acid, acetic acid, boric acid, and various mixed phosphate buffers including combinations of $Na_2HPO_4$ and $NaH_2PO_4$; viscosity modifiers such as hydroxyethyl cellulose, carboxymethyl cellulose, sodium carboxymethyl cellulose, polyvinyl alcohol, polyacrylamide and polyvinyl pyrrolidone; disinfecting agents such as polyquaternary amines, e.g., Croquat TM which is commercially available from Croda, Inc., biguanides, polymeric biguanides such as polyhexamethylene biguanide, available as Cosmocil ® CQ from ICI Americas, peroxide, and water soluble cationic polymers (WSCPs); stabilizing agents, preservatives, etc. The inventive method inhibits the growth of protozoa in any eye care product which is capable of supporting protozoans.

Methods of the invention can also be practiced by adding a solid dosage form, such as a tablet, containing the chelating agent to an eye care solution. Typical tablets to which the chelating agent can be added include cleaning, disinfecting and/or neutralizing tablets. Such tablets can contain, in addition to the chelating agents, excipients well known to those skilled in the art including salts; buffers; effervescing agents, such as tartaric or citric acid used in combination with a suitable alkali metal salt such as sodium carbonate; binders such as starch and gelatin acacia; lubricants such as stearic acid and talc; carriers; fillers; and others normally used in producing tablets.

Protozoan growth on the surfaces of eye care products such as contact lenses and contact lens cases can also be inhibited according to the invention. Such products are placed in contact with a solution containing the chelating agent. Contact lenses can be immersed in a solution containing the chelating agent, for example, while contact lens cases can be at least partially filled with such solutions.

The invention is further illustrated by the following non-limiting examples:

EXAMPLE 1

Inhibition of Acanthamoebal Growth in Growth Media

The effect of addition of EDTA on the growth of *A. polyphaga* trophozoites and on the excystment and outgrowth of *A. polyphaga* cysts in peptone yeast extract glucose (712) broth was investigated. Serial two-fold dilutions of EDTA (0.2%–0.00625%) were prepared in 712 broth in plastic flasks. Each test concentration (5 ml/flask) was inoculated with approximately $10^3$ cysts or trophozoites of each strain tested. Flasks were incubated for 28 days at ambient room temperature. Flasks were observed for visible growth at days 7, 14, 21, and 28. Results are shown in Table I.

TABLE I

| % EDTA | Day 7 troph | Day 7 cyst | Day 14 troph | Day 14 cyst | Day 21 troph | Day 21 cyst | Day 28 troph | Day 28 cyst |
|---|---|---|---|---|---|---|---|---|
| none | + | + | + | + | + | + | + | + |
| 0.00625 | + | + | + | + | + | + | + | + |
| 0.0125 | + | + | + | + | + | + | + | + |
| 0.025 | + | +/− | + | + | + | + | + | + |
| 0.05 | +/− | − | − | − | − | − | − | − |
| 0.1 | − | − | − | − | − | − | − | − |
| 0.2 | − | − | − | − | − | − | − | − |

+: large numbers (>100) present
+/−: very few (<50) present
−: none present

As is clear from Table I, the growth of *A. polyphaga* trophozoites was inhibited by EDTA at concentrations ≧0.05%. Excystment and outgrowth of *A. polyphaga* cysts was also inhibited by EDTA at concentrations ≧0.05%.

Use of chelating agents, such as EDTA, inhibits protozoan growth in commercial eye care product formulations in the same manner.

The following examples give solid and solution compositions including protozoan growth-inhibiting agents within the present invention. Amounts are given in weight % based on the total weight of the tablet. Tablets are typically dissolved in 10 ml of liquid, but can be dissolved in greater or lesser amounts to afford desired concentrations of the chelating agent.

EXAMPLE 2

Enzymatic Cleaning Tablet

| | |
|---|---|
| Papain | 6.7 wt % (activity 2.4–4.0 wpu/tablet) |
| L-Cysteine HCl | 6.7 |
| Disodium EDTA | 5.3 |
| Sodium chloride | 30.0 |
| Sodium borate | 14.0 |
| Sodium carbonate | 20.7 |
| Polyethylene glycol 3350 | 2.7 |
| Tartaric acid | 13.3 |

The tablet is used to clean contact lenses of protein deposits.

EXAMPLE 3

Neutralizing Tablet

| | |
|---|---|
| Disodium EDTA | 10.00 |
| Sodium chloride | 71.42 |
| Hydroxypropyl methylcellulose | 5.5 |
| Catalase | 1.0 |
| Sodium phosphate dibasic | 12.0 |
| Sodium phosphate monobasic | 0.08 |

The tablet is used to neutralize hydrogen peroxide resulting in a storage solution.

EXAMPLE 4

Neutralizing Tablet with Indicator

| | |
|---|---|
| Disodium EDTA | 10.00 |
| Sodium chloride | 71.4115 |
| Hydroxypropyl methylcellulose | 5.5 |
| Catalase | 1.0 |
| Sodium phosphate dibasic | 12.0 |
| Sodium phosphate monobasic | 0.08 |

-continued

| | |
|---|---|
| Vitamin B-12 | 0.0085 |

EXAMPLE 5

Preserved Saline Solution

| | |
|---|---|
| Disodium EDTA | 0.10 |
| Sodium chloride | 0.85 |
| Boric acid | 0.10 |
| Purogene | 0.005 |
| Distilled water | balance |

The solution is used to clean, disinfect and store contact lenses. Purogene is a stabilized $ClO_2$ complex available, for example, from BioCide (Norman, Okla.).

EXAMPLE 6

Buffered Saline Solution

| | |
|---|---|
| Disodium EDTA | 0.10 |
| Sodium chloride | 0.85 |
| Boric acid | 0.10 |
| Distilled water | balance |

The solution is used to rinse, heat and store contact lenses after heat disinfection.

The polyvalent chelating agents within the invention are observed to inhibit the growth of protozoa in eye care compositions such as those exemplified above without need for additional anti-microbial agents.

What is claimed is:

1. A method for inhibiting the growth of protozoa in an eye care product which comprises the step of adding to said eye care product an effective protozoan growth-inhibiting amount of a polyvalent cation chelating agent, whereby protozoan growth is inhibited.

2. A method as claimed in claim 1, wherein said method is effective against protozoa selected from the group consisting of *A. polyphaga, A. castellanii, A. lenticulata, A. hatchetti, A. astronyxis, A. culbertsoni* and *A. rhysodes*.

3. A method as claimed in claim 1, wherein said polyvalent cation is a cation which serves as a cofactor in an enzyme necessary for metabolism in a protozoan.

4. A method as claimed in claim 3, wherein said polyvalent cation is selected from the group consisting of calcium, magnesium, iron, manganese, zinc, copper and nickel cations.

5. A method as claimed in claim 1, wherein said chelating agent is selected from the group consisting of EDTA, CDTA, HEDTA, DTPA. 1,2diaminocyclohexane tetraacetate, and hexametaphosphate.

6. A method as claimed in claim 5, wherein said chelating agent is EDTA.

7. A method as claimed in claim 6, wherein said EDTA is employed in an amount from about 0.05% by weight to about 0.5% by weight.

8. A method as claimed in claim 1, wherein said eye care product is a solution.

9. A method as claimed in claim 8, wherein said eye care product is a contact lens solution selected from the group consisting of a saline solution, a rinsing solution, a neutralizing solution, a cleaning solution, a storage solution and a lubricating/wetting solution.

10. A method as claimed in claim 1, wherein said eye care product is an eye care solution and said chelating agent is added to said solution in a tablet formulation.

11. A method for inhibiting the growth of protozoa on a surface of an eye care product which comprises the step of contacting said eye care product with a solution comprising an effective protozoan growth-inhibiting amount of a polyvalent cation chelating agent.

12. A method as claimed in claim 11, wherein said eye care product is a contact lens or a contact lens case.

13. A method as claimed in claim 11, wherein said method is effective against protozoa selected from the group consisting of *A. polyphaga, A. castellanii, A. lenticulata, A. hatchetti, A. astronyxis, A. culbertsoni* and *A. rhysodes*.

14. A method as claimed in claim 11, wherein said polyvalent cation is a cation which serves as a cofactor in an enzyme necessary for metabolism in a protozoan.

15. A method as claimed in claim 14, wherein said polyvalent cation is selected from the group consisting of calcium, magnesium, iron, manganese, zinc, copper and nickel cations.

16. A method as claimed in claim 11, wherein said chelating agent is selected from the group consisting of EDTA, CDTA, HEDTA, DTPA, 1,2-diaminocyclohexane tetraacetate, and hexametaphosphate.

17. A method as claimed in claim 16, wherein said chelating agent is EDTA.

18. A method as claimed in claim 17, wherein said EDTA is employed in an amount from about 0.05% by weight to about 0.5% by weight.

* * * * *